United States Patent [19]

Kalman et al.

[11] 4,339,441
[45] Jul. 13, 1982

[54] CARDIOACTIVE FACTOR

[75] Inventors: Sumner M. Kalman, 2299 Tasso, Palo Alto, Calif. 94301; Ruth M. Jones, Redwood City, Calif.

[73] Assignee: Sumner M. Kalman, Redwood City, Calif.

[21] Appl. No.: 316,926

[22] Filed: Oct. 30, 1981

[51] Int. Cl.³ .................. A61K 37/00; A61K 35/14
[52] U.S. Cl. .................................. 424/177; 424/101; 260/112 R
[58] Field of Search .............................. 424/101, 177; 260/112 R

[56] References Cited

U.S. PATENT DOCUMENTS 4,237,046 12/1980 Bodanszky ..................... 424/177

Primary Examiner—Sam Rosen
Attorney, Agent, or Firm—Burns, Doane, Swecker & Mathis

[57] ABSTRACT

A proteinaceous cardioactive factor that exhibits positive inotropic activity and positive chronotropic activity has been partially extracted from mammalian plasma by precipitation with polyethylene glycol followed by cation exchange chromatography. The factor may be fractionated into two active fractions, one having an apparent molecular weight of about 130,000 daltons and the other having an apparent molecular weight of about 30,000 daltons, by gel filtration chromatography.

12 Claims, No Drawings

CARDIOACTIVE FACTOR

TECHNICAL FIELD

The invention is a cardioactive factor that has been found to be present in mammalian blood and that has been discovered to have inotropic and chronotropic activities similar to digitalis.

BACKGROUND ART

Digitalis, a plant derivative not believed to be native to mammals, is the most commonly used drug in the treatment of heart failure. It exhibits positive inotropic and positive chronotropic activities. Despite its widespread use, however, it has an unfavorable therapeutic index and frequently causes toxicity in patients.

The description of blood components that possess positive inotropic activity goes back at least to Bowditch's 1871 report of the inotropic effect of plasma on isolated frog heart. The existence of an endogenous substance in blood that simulates the therapeutic effect of digitalis was postulated in 1952 by Szent-Gyorgyi, *Chemical Physiology of Contraction in Body and Heart Muscle*, pp. 88–89, Academic Press, Inc., New York (1953). His colleague, Hadju continued to search for the substance without success. Hadju and Leonard recently reported a system of at least five high molecular weight (>130,000 daltons) proteins that affect access of calcium to contractile tissue of muscle, but has no special predilection for cardiac muscle, *J Cell Physiol* 96, 279–80 (1978). These proteins allegedly interact in a given sequence in such a way that the transport of calcium ions into the cell is enhanced, and a positive inotropic response is obtained. A group of small peptides with cardioactive effects in vitro were isolated by Naylor and Lowe, Am Heart J 1965; 69: 1–3. Called "kinekards," these peptides apparently have low molecular weights (4000-8000 daltons). They exhibit positive inotropic and pressor effects and increase the rate of oxidative metabolism, Lowe, Australas Ann Med 1969; 18: 108–112. Endogenous ligands of low molecular weight that have strong affinity for sodium-potassium adenosine triphosphatase (Na-K ATPase) have been reported, Fishman, M.C., PNAS USA (1979) 76: 4661–4663, and Garner, TH, Jr., et al., PNAS USA (1979) 76: 4658–4660. These ligands were isolated from brain or hypothalamus and were characterized by a molecular weight below 2500 daltons and by its affinity for Na-K ATPase. These reports did not indicate whether the ligands possessed any cardioactive properties.

DISCLOSURE OF INVENTION

The present invention concerns a substance that has a digitalis-like cardioactivity and exists in human blood but heretofore has not been recognized, isolated, purified or characterized chemically. This substance is sometimes referred to herein as a "cardioactive factor." Although the chemical composition and structure of this cardioactive factor has not yet been defined specifically, it is characterized by the following principal properties.

Chemical and Physical Properties (1) insoluble in 10% (w/v) polyethylene glycol, 6000 mw, at 4° C. and at room temperature (20°-25° C.);

(2) elutable from ion exchange carboxymethyl cellulose with 0.5 M NaCl at pH 5;

(3) separable by agarose gel filtration into two fractions, one having an apparent molecular weight of about 130,000 daltons and the other having an apparent molecular weight of about 30,000 daltons.

Biochemical and Biological Properties (1) has both positive inotropic and positive chronotropic activities (both fractions mentioned above have such activities) that are labile at 0° C. and are relatively stable at 25° C. and 40° C.; and (2) achieves peak positive inotropic activity before peak positive chronotropic activity Based on present data concerning the factor it is believed to be a globular protein that may occur in two different molecular forms, such as a monomer and oligomer, that differ in molecular weight and exhibit the same kind of cardioactivity.

The factor in a concentrated but impure extract may be derived from mammalian blood plasma such as human and bovine plasma by precipitation with polyethylene glycol or other globulin-fibrinogen precipitant (the precipitant contains a small amount of albumins) and cation exchange fractionation. The concentrated extract may be fractionated into the above-described molecular forms by gel filtration. More specifically, plasma from a mammal has been treated with polyethylene glycol at concentrations that separate the albumins from the globulins and fibrinogen. The globulin-fibrinogen precipitate is then put into solution and applied to a carboxymethyl cellulose ion exchange column at pH 5. The factor is retained on the column at that pH. It is then eluted with 0.5 M NaCl and reprecipitated to separate it from the salt. The precipitate is then put into solution and concentrated by ultrafiltration using a filter that generally retains substances having molecular weights greater than about 100,000 daltons. (Molecular shape and adsorption may cause retention of smaller molecules also). The concentrate may then be fractionated into a first fraction having a mol wt of about 130,000 and a second fraction having a mol wt of about 30,000 by gel filtration chromatography on an agarose column.

The following examples and tests further illustrate the partial extraction of the cardioactive factor from blood and its properties.

EXAMPLE 1

Preparation of Cardioactive Factor Extract

Bovine blood was collected at a local slaughterhouse and 2500 units of heparin per liter was added to it. The heparinized blood was centrifuged at 5,000×g for 30 minutes at 25° C. The plasma was decanted. Polyethylene glycol 6000 (PEG) was obtained from the J. T. Baker Chemical Company (Phillipsburg NJ) or the Sigma Chemical Company (St. Louis, MO). A 20% (w/v) solution was made with glass-distilled water.

The heparinized bovine plasma was treated with an equal volume of 20% PEG (final concentration of PEG=10%). The suspension was stirred for 10 minutes then centrifuged at 6,000×g for 10 minutes. The supernatant solution was discarded and the precipitate washed with glass-distilled water. The precipitate was redissolved in a buffer containing sodium phosphate $5 \times 10^{-2}$ M, 20% glycerol and disodium edetate (EDTA) $10^{-3}$ M at pH 5.0. The volume of buffer used was equal to the original volume of plasma. This mixture was then clarified by centrifugation for 10 minutes at 5,000×g.

Cation exchange was performed on carboxymethyl cellulose (CM52, Whatman Biochemicals, Ltd., England). The cellulose was equilibrated in sodium phosphate $5 \times 10^{-2}$ M buffer containing 20% glycerol and EDTA, $10^{-3}$ M, at pH 5.0. The cation exchange was done by a batch method. One volume of the redissolved PEG precipitate was added, with stirring, to one-half volume of the cellulose in a beaker (the settled volume of the cellulose suspended in buffer, was measured). The suspension was stirred for 15 minutes. it was then filtered on a Buchner funnel, and rinsed once with one volume of the phosphate buffer. Because PEG is uncharged, it was removed by this step. The cellulose was eluted successively with NaCl (0.1 M and 0.5 M) added to the starting buffer using buffer volumes equal to twice that of the cellulose for each step. The cellulose was stirred for 15 minutes with the buffer, then filtered.

The fraction eluted with 0.5 M NaCl was concentrated by ultrafiltration using an Amicon XM100A membrane (Amicon Corp, Lexington, MA) under nitrogen pressure (25 psi) in an Amicon Model 52 stir cell. This concentrate and the starting heparinized bovine plasma were bioassayed for inotropic and chronotropic activity by the following procedure.

Bioassay Procedure

Materials were tested on isolated, spontaneously beating guinea pig atria in an aerated four ml muscle bath by the procedure described by applicants in Gen Pharmacol 11:463–457 (1980), which disclosure is incorporated herein by reference. The phosphate buffers and excess NaCl, if any, in the same materials were removed by buffer exchange to Krebs' bicarbonate/Ringer's solution using Sephadex G-25 columns. Amplitude and rate of contraction were recorded via a force transducer connected through a preamplifier to a recorder (Grass Instruments, Quincy, MA). Inotropic responses of the atrial preparation were standardized for each experiment with graded doses of norepinephrine. Inotropic responses of the atria to test materials were assayed relative to the inotropic activity of one nmol of norepinephrine. Chronotropic responses were measured as the increase in beats per minute over the control rate.

The results of the bioassays respecting inotropic activity are reported in Table 1 below. An inotropic activity unit (IAU) is defined as the amount of a substance with the same inotropic activity as 1 nmol norepinephrine.

TABLE 1

|  | Protein (mg) | Inotropic activity (IAU) | Specific activity (IAU/mg) |
|---|---|---|---|
| Bovine plasma (425 ml) | 53,125 | 72.2 | 0.0014 |
| Cation exchange | 2,604 | 54.6 | 0.021 |

EXAMPLE 2

Bovine plasma was treated as in Example 1 to prepare a concentrated extract. Gel filtration chromatography was performed on the extract using a 1.6×51 cm column of Bio-Gel A-0.5 m agarose (Bio-Rad Laboratories, Richmond, CA). The bed volume was 102 ml. The column was equilibrated with the buffer, 0.05 M sodium phosphate with 20% glycerol, 0.1 M NaCl and EDTA, $10^{-2}$ M, at pH 7.4. The flow rate of the column was 0.9 ml per minute. The column was calibrated with molecular weight markers in order to estimate the apparent molecular weight of the fractions. Five ml fractions were collected using the same buffer as described above plus 8 M urea. The starting bovine plasma and each of the fractions were bioassayed for inotropic activity by the procedure described in Example 1. Two of the fractions, one having a mol wt of about 130,000 daltons and the second having a mol wt of about 30,000 daltons, exhibited high positive inotropic activity.

The results of these assays on the two fractions and the starting plasma are reported in Table 2 below. Total activity is expressed as a proportion of the positive inotropic activity of one ml of the starting plasma which was arbitrarily assigned an activity value of 100.

TABLE 2

|  | Total Activity | Total Protein | Spec. Act. (Total Act./ Total Protein) |
|---|---|---|---|
| Plasma (100 ml) | 100 | 8000 | 0.01 |
| Agarose |  |  |  |
| eluate 130,000d | 20 | 90 | 0.31 |
| eluate 30,000d | 28 | 13 | 2.15 |

EXAMPLE 3

Freshly frozen human plasma was thawed and treated as was the bovine plasma in Example 1 except that the fraction eluted from the cation exchange column with 0.5 M NaCl was not ultrafiltered. Instead, that eluate was precipitated with PEG, taken up in 20 mM phosphate buffer (pH 7) and then applied to a 1.6×51 cm diethylaminoethyl cellulose anion exchange column (DE52, Whatman Biochemicals, Ltd.) The column was washed with buffer until it was free of PEG. Elution was carried out with an NaCl gradient from 0 to 0.3 M. The starting plasma, the cation exchange eluate and the anion exchange eluate fractions were bioassayed by the procedure of Example 1. The results of these assays are shown in Table 3 below. A unit of activity is defined as the inotropic response of one ml of plasma from which serotonin and other small molecules had been removed by gel filtration using a Sephadex G-25 column. The reported DE 52 eluate is that fraction collected at 0.20–0.25 M NaCl

TABLE 3

| Material | Total protein mg | Total activity units | Specific activity, units/mg |
|---|---|---|---|
| Plasma (50 ml) | 3800 | 50 | 0.013 |
| CM 52 eluate | 490 | 49 | 0.10 |
| DE 52 eluate | 18 | 6 | 0.33 |

Relative to norepinephrine the gel filtered plasma had a positive inotropic effect of 14%. The maximal effects of the DE52 eluate collected using 0.20–0.25 M NaCl were 50% of the maximal inotropic response to norepinephrine and nearly 90% of the maximal chronotropic responese to norepinephrine. These effects took three to ten minutes to develop fully and required 15 to 20 minutes to subside. The time required for maximal response to develop was longer than that for serotonin, norepinephrine, and calcium. The tracings of the responses to the cardioactive factor obtained in the above described tests indicate that following administration of the factor, peak positive inotropic activity occurs before peak chronotropic activity.

The ion exchange chromatography results reported in Example 3 suggests that the cardioactive factor has an isoelectric point between pH 5 and pH 7.

Temperature stability tests on the concentrated extract indicated that the inotropic and chronotropic activities of the factor were stable when the extract was frozen. In contrast both activities were labile at 0° C., with the inotropic activity being the more labile of the two. Stability at 0° C. was enhanced by glycerol, 20% v/v, and by disodium edetate $10^{-3}$ M. Heating block studies at temperatures above 0° C. indicated that both activities were most stable at 25° C. and 40° C. Both activities were destroyed by heating the extract in a boiling water bath for ten minutes.

It was also observed that the addition of propanolol at $10^{-6}$ M concentration to the atrial bath blocked the positive inotropic and positive chronotropic activities of norepinephrine, but had no effect on the activities of the cardioactive factor. This indicates that the receptors for the cardioactive factor may be different from the receptors for norepinephrine.

Based on the movement of the two activities together through the partial purification steps described above, applicants currently believe the chronotropic and inotropic activities exhibited by the partially purified factor derive from one protein molecule. In this regard the two activities may represent different active sites on one molecule, different subunits of a single large molecule, or a small active peptide bound tightly to a larger carrier protein.

It is expected that further purification of the extract described above will result in isolation of pure or substantially pure cardioactive factor. Such purification will likely be achieved by the conventional gel filtration, ion exchange chromatography, high performance liquid chromatography and other fractionation techniques normally used to isolate individual proteins from mammalian fluids or cells. Following purification of the factor, its chemical, physical, and biological properties may be further characterized by conventional methods. For instance, primary structure of a protein may be determined by sequential enzymatic cleavage of the protein into individual amino acids and analysis of those amino acids.

The data presented above suggest the usefulness of the factor as a cardioactive agent to manage heart conditions in humans or other mammals, such as disrythmia and heart failure. If used in such therapy the factor will be administered, typically parenterally, in a dose that is sufficient to cause a positive inotropic effect. For parenteral administration the factor will be formulated in a unit dosage injectable form (solution, suspension, emulsion) in association with a pharmaceutically acceptable parenteral vehicle. Such vehicles are inherently nontoxic and nontherapeutic. Examples of such vehicles are water, saline, Ringer's solution, dextrose solution and Hank's solution. The vehicle may contain minor amounts of additives such as substances that enhance isotonicity or the stability of the factor. Based upon the concentration of the factor that affected the isolated pig atria in the tests described above and the amount of the digitalis glycoside, ouabain, that caused equivalent effects in similar tests, it is estimated that a therapeutically effective dose of the factor for a 70 kg person will range between about 20 to 200 mg (or about 0.3 to 3 mg/kg of body weight). The projected regimen to maintain therapy is once daily or perhaps more often depending upon the duration of activity of the factor. As indicated, these dose estimates are based on in vitro results and it is quite likely that smaller doses will suffice in an intact animal where a normal physiological milieu is maintained. In addition to therapeutic use, the factor may also be used as an analyte for diagnosis of heart conditions or monitoring of therapy.

Modifications and variations in the cardioactive factor, its preparation, and use that are obvious to those of skill in the chemical, biochemical and/or medical arts are intended to be within the scope of the following claims.

We claim:

1. A proteinaceous cardioactive factor endogenous to mammalian blood that:
    a. is insoluble in 10% w/v polyethylene glycol, 6000 mw, at 4° C. and at room temperature;
    b. is elutable from ion exchange carboxymethyl cellulose with 0.5 M NaCl at pH 5;
    c. has both positive inotropic and positive chronotropic activities that are labile at 0° C. and relatively stable at 25° C. and 40° C.;
    d. is separable by agarose gel filtration into two fractions, one of which has an apparent molecular weight of about 130,000 daltons and the other of which has an apparent molecular weight of about 30,000 daltons, and both of which exhibit said activities; and
    e. achieves peak positive inotropic activity before peak positive chronotropic activity.

2. A cardioactive factor prepared from mammalian blood plasma by:
    a. fractionating the plasma by precipitation into a globulin-fibrinogen precipitate and an albumin supernatant;
    b. applying the precipitate in solution at a pH of about 5 to a cation exchange material;
    c. eluting the factor from the cation exchange material with 0.5 M sodium chloride; and
    d. removing sodium chloride from the eluate.

3. The cardioactive factor of claim 2 wherein the mammalian blood plasma is bovine blood plasma or human blood plasma.

4. The cardioactive factor of claim 2 wherein the preparation includes:
    e. subjecting the eluate to gel filtration to produce a fraction having an apparent molecular weight of about 30,000 daltons.

5. The cardioactive factor of claim 2 wherein the preparation includes:
    e. applying the eluate at a pH of about 7 to an anion exchange material;
    f. eluting the factor from the anion exchanger material by gradient elution with 0.2 to 0.25 M sodium chloride, and
    g. removing the sodium chloride from the eluate of step f.

6. The cardioactive factor of claim 2 wherein the cation exchange material is carboxymethyl cellulose.

7. The cardioactive factor of claim 5 wherein the cation exchange material is carboxymethyl cellulose and the anion exchange material is diethylaminoethyl cellulose.

8. A method for treating a mammal for a cardiac condition comprising administering a therapeutically effective amount of the cardioactive factor of claim 1 or 2 to the mammal.

9. The method of claim 8 wherein the amount is sufficient to produce a positive inotropic effect on the heart of the mammal.

10. The method of claim 8 wherein the administration is parenteral.

11. The method of claim 8 wherein the mammal is a human.

12. A cardioactive composition for treating a mammal for a heart condition comprising a therapeutically effective amount of the cardioactive factor of claim 1 or 2 associated with a pharmaceutically acceptable parenteral vehicle.

* * * * *